US00PP23909P2

(12) United States Plant Patent
Smith

(10) Patent No.: US PP23,909 P2
(45) Date of Patent: Sep. 17, 2013

(54) ***CHRYSANTHEMUM* PLANT NAMED 'CIFZ0019'**

(50) Latin Name: *Chrysanthemum×morifolium*
Varietal Denomination: CIFZ0019

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 65 days.

(21) Appl. No.: 13/385,183

(22) Filed: Feb. 6, 2012

(51) Int. Cl.
*A01H 5/00* (2006.01)

(52) U.S. Cl.
USPC ..... Plt./291

(58) Field of Classification Search
USPC ..... Plt./291
See application file for complete search history.

*Primary Examiner* — Annette Para
(74) *Attorney, Agent, or Firm* — Joshua L. Price

(57) ABSTRACT

A new *Chrysanthemum* plant named 'CIFZ0019' particularly distinguished by the small light red to orange-red over yellow decorative inflorescences with medium yellow-green foliage, compact and mounded plant habit with a mid to late September natural flowering season.

1 Drawing Sheet

Latin name of the genus and species of the plant claimed: *Chrysanthemum×morifolium.*

Varietal denomination: 'CIFZ0019'.

BACKGROUND OF THE NEW PLANT

The present invention comprises a new *Chrysanthemum*, botanically known as *Chrysanthemum×morifolium*, and hereinafter referred to by the variety name 'CIFZ0019'.

'CIFZ0019' is a product of a planned breeding program. The new cultivar has small light red to orange-red over yellow decorative inflorescences with medium yellow-green foliage, compact and mounded plant habit with a mid to late September natural flowering season.

'CIFZ0019' originates as a natural whole plant mutation of 'CIFZ0021'. 'CIFZ0019' was discovered and selected by the inventor as a single flowering plant within a large population of the parent cultivar grown massed in pots outdoors in a controlled breeding program in Alva, Fla. in November 2009. The parent cultivar 'CIFZ0021' has dark pink inflorescence color with a block cloth flowering response that is slower than 'CIFZ019'.

The first act of asexual reproduction of 'CIFZ0019' was accomplished when vegetative cuttings were propagated from the initial selection in January 2010 in a greenhouse in Alva, Fla.

BRIEF SUMMARY OF INVENTION

Horticultural examination of plants grown from cuttings of the plant initiated in January 2010, and continuing thereafter, has demonstrated that the combination of characteristics as herein disclosed for 'CIFZ0019' are firmly fixed and are retained through successive generations of asexual reproduction.

'CIFZ0019' has not been observed under all possible environmental conditions. The phenotype may vary significantly with variations in environment such as temperature, light intensity, and day length.

Plant Breeder's Rights for this cultivar were applied for in Canada on Feb. 24, 2011, No. 11-718 and at the Community Plant Variety office on Mar. 30, 2011, No. 2011/0792.

'CIFZ0019' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0019' with colors being as true as possible with an illustration of this type.

The photographic drawing shows a flowering potted plant of the new variety, and a close-up of the flowers.

DETAILED BOTANICAL DESCRIPTION

The plant descriptions, measurements and aforementioned photograph were taken outdoors in Gilroy, Calif. in August 2011. The plants were growing in an outdoor potted plant trial, in one gallon pots, in full sun. These plants were about 12 weeks old.

Color references are made to The Royal Horticultural Society Colour Chart (R.H.S.) 2001.

TABLE 1

DIFFERENCES BETWEEN THE NEW VARIETY 'CIFZ0019' AND A MOST SIMILAR VARIETY

| | 'CIFZ0019' | 'Zesty Yovictoria' (U.S. Plant Pat. No. 15,323) |
|---|---|---|
| Inflorescence size: | Smaller | Little larger |
| Plant size: | Smaller overall | Larger |
| Black cloth flowering response: | Slower | Faster |

Plant:

*Form, growth and habit.*—Herbaceous garden-type, stems upright and outwardly spreading, freely branching.

*Plant height.*—15.0 cm.

*Plant height (inflorescence included).*—17.0-18.0 cm.
*Plant width.*—33.0-35.0 cm.

Roots:
*Number of days to initiate roots.*—About 4 days at about 22 degrees C.
*Number of days to produce a rooted cutting.*—4-6 days at 22 degrees C.
*Type.*—Fine, fibrous, free branching.
*Color.*—RHS N155B but whiter.

Foliage:
*Arrangement.*—Alternate.
*Immature, leaf color, upper surface.*—Closest to RHS 146a but a little darker.
*Lower surface.*—RHS 137C but appears greyer due to hairs.
*Mature, leaf color, upper surface.*—Closest to RHS 146A but a little darker.
*Lower surface.*—RHS 137C but appears greyer due to hairs.
*Length.*—2.6-3.3 cm.
*Width.*—2.0-2.5 cm.
*Shape.*—Ovate.
*Base shape.*—Attenuate.
*Apex shape.*—Acute.
*Margin.*—Irregularly incised or partly cleft; entire.
*Texture, upper surface.*—Bifid T-shaped hairs.
*Lower surface.*—Bifid T-shaped hairs.
*Color of veins, upper surface.*—RHS 144B becoming indistinct.
*Color of veins, lower surface.*—RHS 144B.
*Petiole color.*—RHS 144B.
*Length.*—0.7-1.0 cm.
*Diameter.*—0.15-0.2 cm.
*Texture.*—Bifid T-shaped hairs.

Stem:
*Quantity of main branches per plant.*—7-10.
*Color of stem.*—Between RHS 146A and RHS 146B.
*Length of stem.*—8.0-10.0 cm.
*Diameter.*—0.4 cm.
*Length of internodes.*—1.0-2.0 cm.
*Texture.*—Bifid T-shaped hairs.
*Color of peduncle.*—Between RHS 146A and RHS 146B.
*Length of peduncle.*—6.0-6.5 cm.
*Peduncle diameter.*—0.15 cm.
*Texture.*—Bifid T-shaped hairs.

Inflorescence:
*Type.*—Compositae, solitary decorative-type inflorescences; borne terminally above foliage, ray florets arranged acropetally on a capitulum.
*Quantity of inflorescences per plant.*—30-40 with 100-125 buds.
*Lastingness of individual blooms on the plant.*—About 6 weeks from first color showing.
*Fragrance.*—Slightly spicy.

Bud (just when opening/showing color):
*Color.*—A slightly subdued hue of RHS 185B.
*Length.*—0.7-0.9 cm.
*Width.*—1.0-1.2 cm.
*Shape.*—Oblate.

Immature inflorescence:
*Diameter.*—2.6-3.2 cm.
*Color of ray florets, upper surface.*—RHS 3B ground color overlaid heavily with a subdued hue of RHS 185B to RHS 185C.
*Lower surface.*—RHS 3B ground color overlaid heavily a subdued hue of RHS 185C.

Mature inflorescence:
*Diameter.*—3.9-4.1 cm.
*Depth.*—0.7-0.9 cm.
*Total diameter of disc.*—Indistinct.
*Receptacle height.*—0.3-0.4 cm.
*Receptacle diameter.*—0.5 cm.

Ray florets:
*Average quantity of florets.*—150 in numerous whorls.
*Color of florets, upper surface.*—Closest to RHS 8B ground color heavily overlaid with between RHS 48C and RHS 54B with RHS 47C to RHS 47D veining. Sometimes appears more orange-red like RHS 32C to RHS 32D with veining of RHS 47C to RHS 47D.
*Lower surface.*—Between RHS14C and RHS 14D overlaid RHS 185D with RHS 185C margins.
*Length.*—1.3-1.5 cm.
*Width.*—0.45-0.55 cm.
*Shape.*—Obovate.
*Apex shape.*—Rounded to a few being irregularly retuse or praemorse.
*Margin.*—Entire.
*Texture, upper surface.*—Papillose.
*Lower surface.*—Papillose.

Disc florets:
*Average quantity of florets.*—8-12.
*Color of florets.*—RHS 13A to RHS 13B, with RHS 1C basally and RHS N34C spots at apex.
*Length.*—0.3 cm.
*Width.*—0.1 cm.
*Shape.*—Tubular, elongated.
*Apex shape.*—Acute, 5 pointed.

Phyllaries:
*Quantity.*—20-25.
*Color, upper surface.*—RHS 138B.
*Lower surface.*—RHS 138A.
*Length.*—0.4-0.5 cm.
*Width.*—0.15 cm.
*Shape.*—Lanceolate.
*Apex shape.*—Acute.
*Base.*—Fused.
*Margins.*—Entire; some with papery edges.
*Texture, upper surface.*—Glabrous.
*Lower surface.*—Bifid T-shaped hairs.

Reproductive organs:
*Pistil.*—1, found on both types of florets.
*Length.*—0.3-0.45 cm.
*Style color.*—Closest to RHS 1C.
*Style length.*—0.2-0.3 cm.
*Stigma color.*—RHS 15B.
*Stigma shape.*—Bi-parted; frilly.
*Ovary color.*—RHS 155C.
*Ovary length.*—0.05 cm.
*Ovary width.*—0.05 cm.
*Stamens.*—4, found on only on the disc florets.
*Color of filaments.*—RHS 1C.
*Length filaments.*—0.2 cm.
*Anthers.*—Not fully formed or are overly mature, or damaged — unable to evaluate.

What is claimed is:

1. A new and distinct variety of *Chrysanthemum* plant named 'CIFZ0019' substantially as illustrated and described herein.

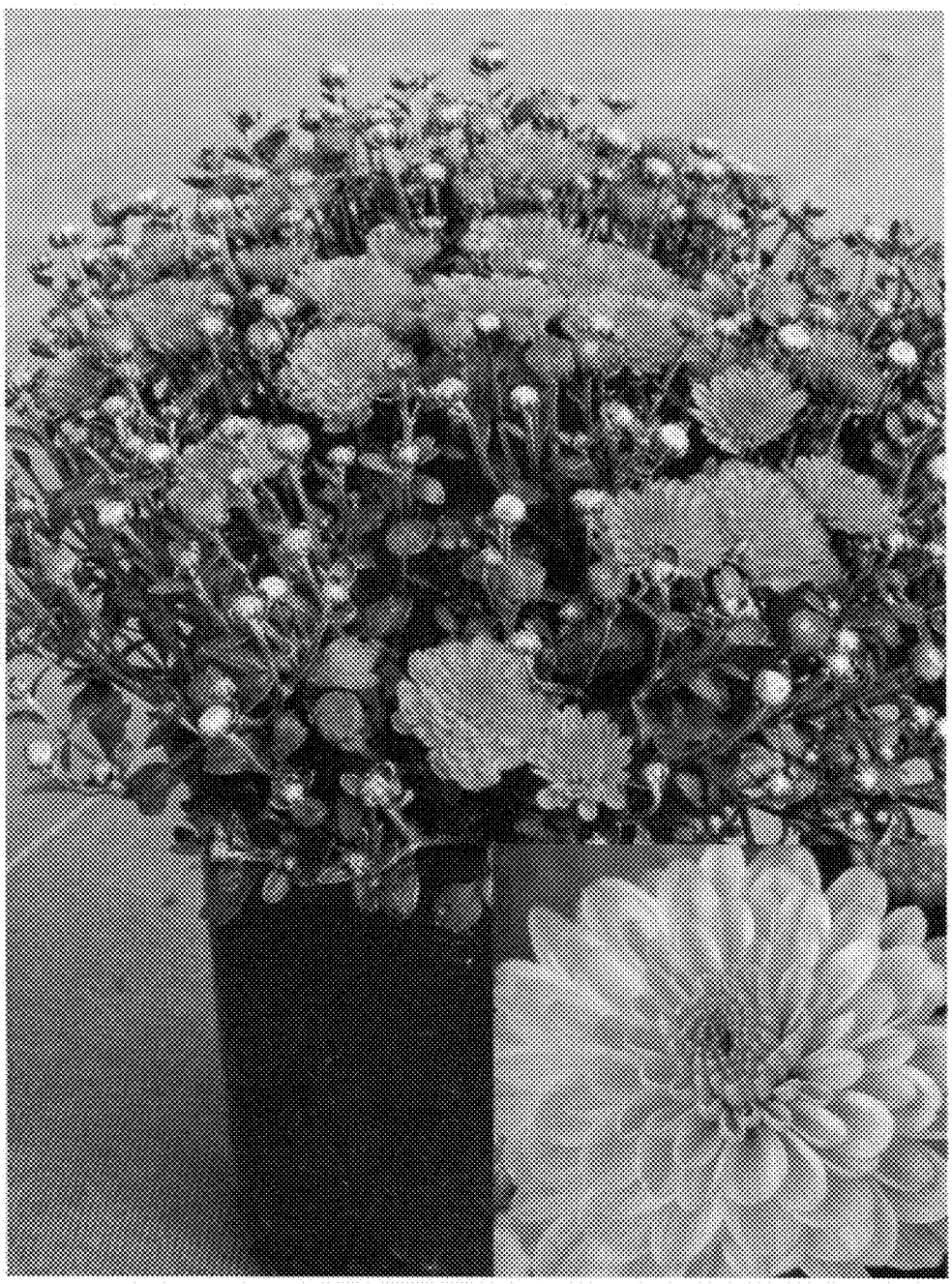

* * * * *